US007335809B2

(12) United States Patent
Riesinger

(10) Patent No.: US 7,335,809 B2
(45) Date of Patent: Feb. 26, 2008

(54) ABSORPTION BODY FOR ATTACHMENT TO THE HUMAN BODY

(76) Inventor: Birgit Riesinger, Zum Holtkamp 3, 48346 Ostbevern (DE)

( * ) Notice: Subject to any disclaimer, the term of this patent is extended or adjusted under 35 U.S.C. 154(b) by 116 days.

(21) Appl. No.: 10/513,262

(22) PCT Filed: May 8, 2003

(86) PCT No.: PCT/EP03/04830

§ 371 (c)(1),
(2), (4) Date: Nov. 2, 2004

(87) PCT Pub. No.: WO03/094813

PCT Pub. Date: Nov. 20, 2003

(65) Prior Publication Data

US 2005/0143697 A1    Jun. 30, 2005

(30) Foreign Application Priority Data

May 8, 2002   (DE) ............................... 202 07 356

(51) Int. Cl.
*A61F 13/15* (2006.01)
(52) U.S. Cl. .................. 604/358; 604/332; 604/367
(58) Field of Classification Search ................ 604/358, 604/332–355, 367
See application file for complete search history.

(56) References Cited

U.S. PATENT DOCUMENTS 3,507,282 A * 4/1970 Burding ...................... 604/333
3,613,123 A * 10/1971 Langstrom .................. 4/144.3
4,886,509 A * 12/1989 Mattsson .................... 604/349
6,186,990 B1 * 2/2001 Chen et al. ................. 604/349
6,530,909 B1 * 3/2003 Nozaki et al. .............. 604/349

FOREIGN PATENT DOCUMENTS

| DE | 3512859 A1 * | 10/1986 |
| DE | 100 59 439 | 8/2001 |
| EP | 1177781 A2 * | 2/2002 |
| WO | WO 200145757 A1 * | 6/2001 |

OTHER PUBLICATIONS

English Translation of DE 10059439 by FLS, Inc. Nov. 2005.*
Englsih Translation of DE 3512859 by McElroy Translation Company. Dec. 2005.*

* cited by examiner

*Primary Examiner*—Tatyana Zalukaeva
*Assistant Examiner*—Ginger Chapman
(74) *Attorney, Agent, or Firm*—Milde & Hoffberg, LLP

(57) ABSTRACT

An absorptive body (50) for attachment to the human body, especially for absorbing fluids coming out of parts of the human body such as wounds, has a substantially flat material section made of an absorbing material (1), which consists of an absorbing non-woven having super-absorber particles spread therein, and a fluid-permeable shell (2) that surrounds the material section, forms a barrier against solid excretions and enables the passage of other excreted substances into the material section made of absorbing material (1) that is arranged inside the shell (2). The shell is made of a small-pored material, whose pores are smaller than the unwetted super-absorber particles.

21 Claims, 13 Drawing Sheets

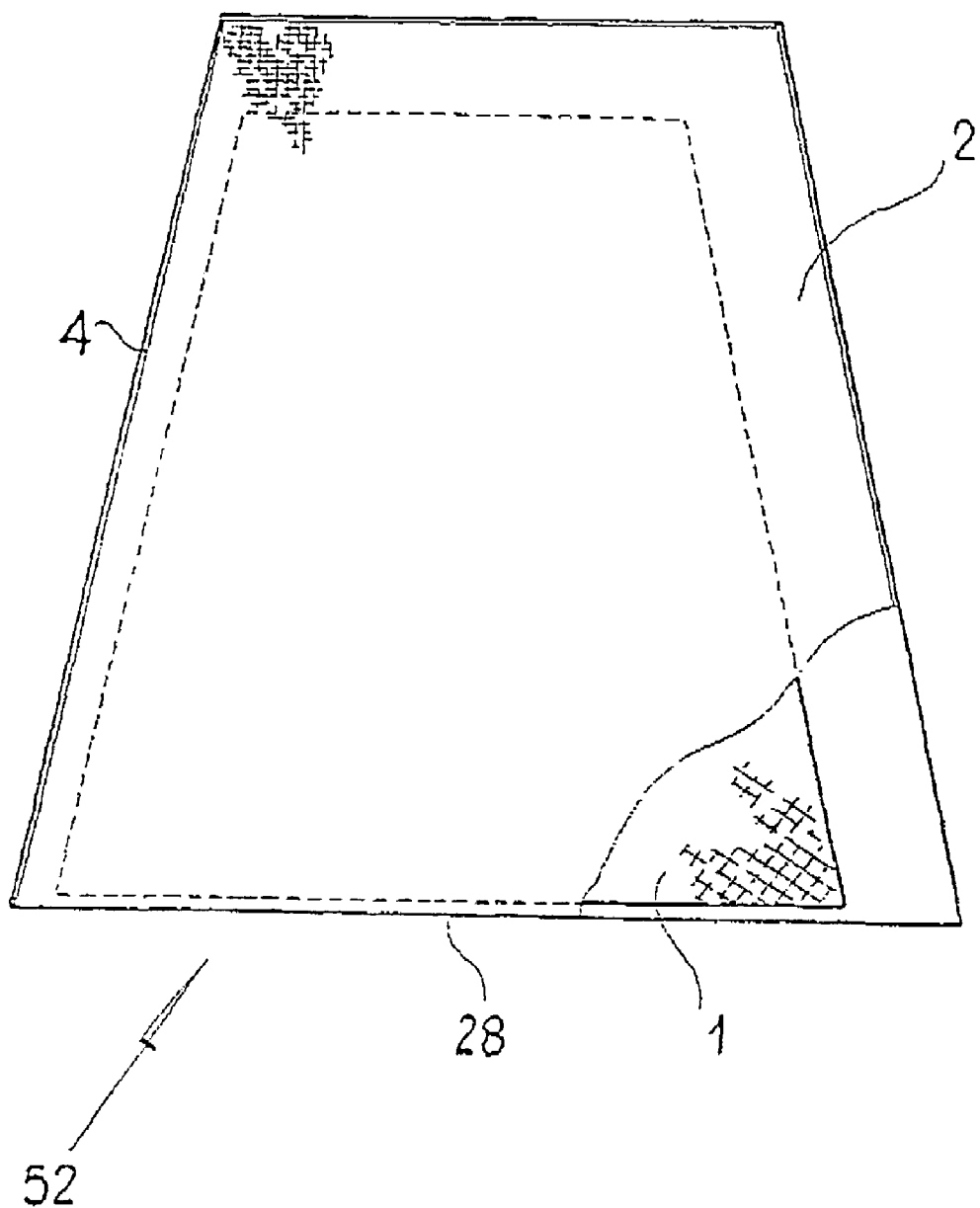

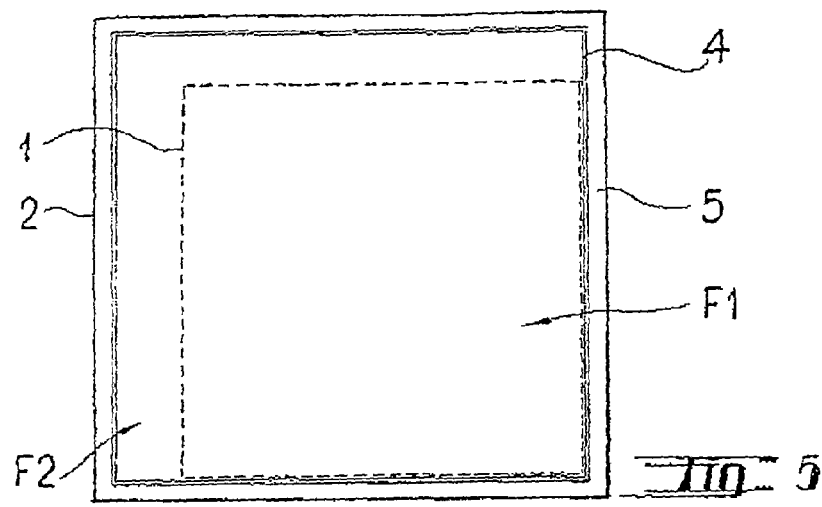
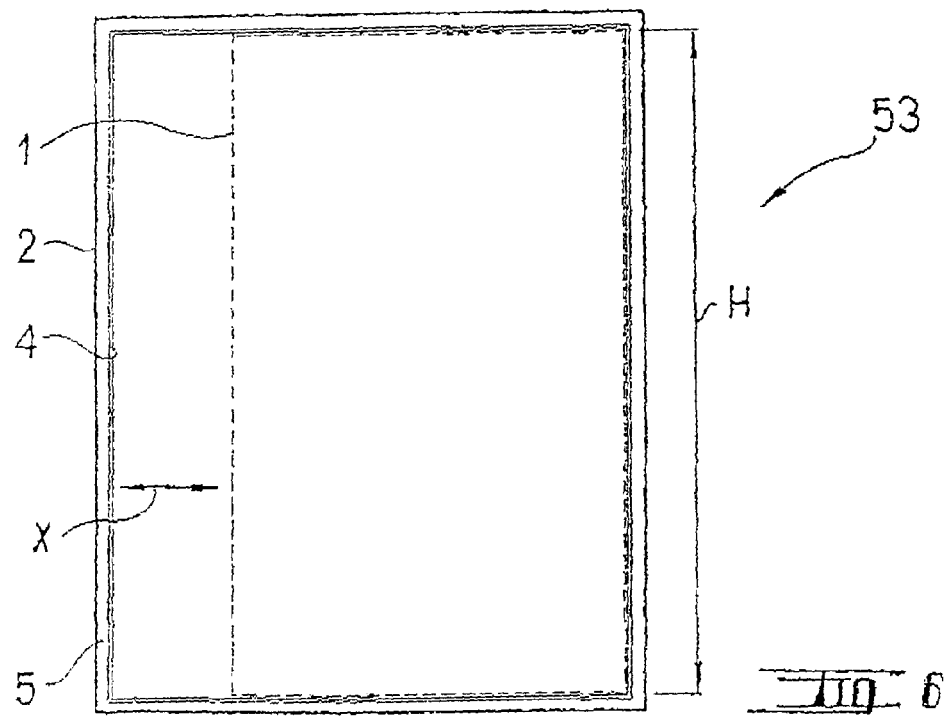

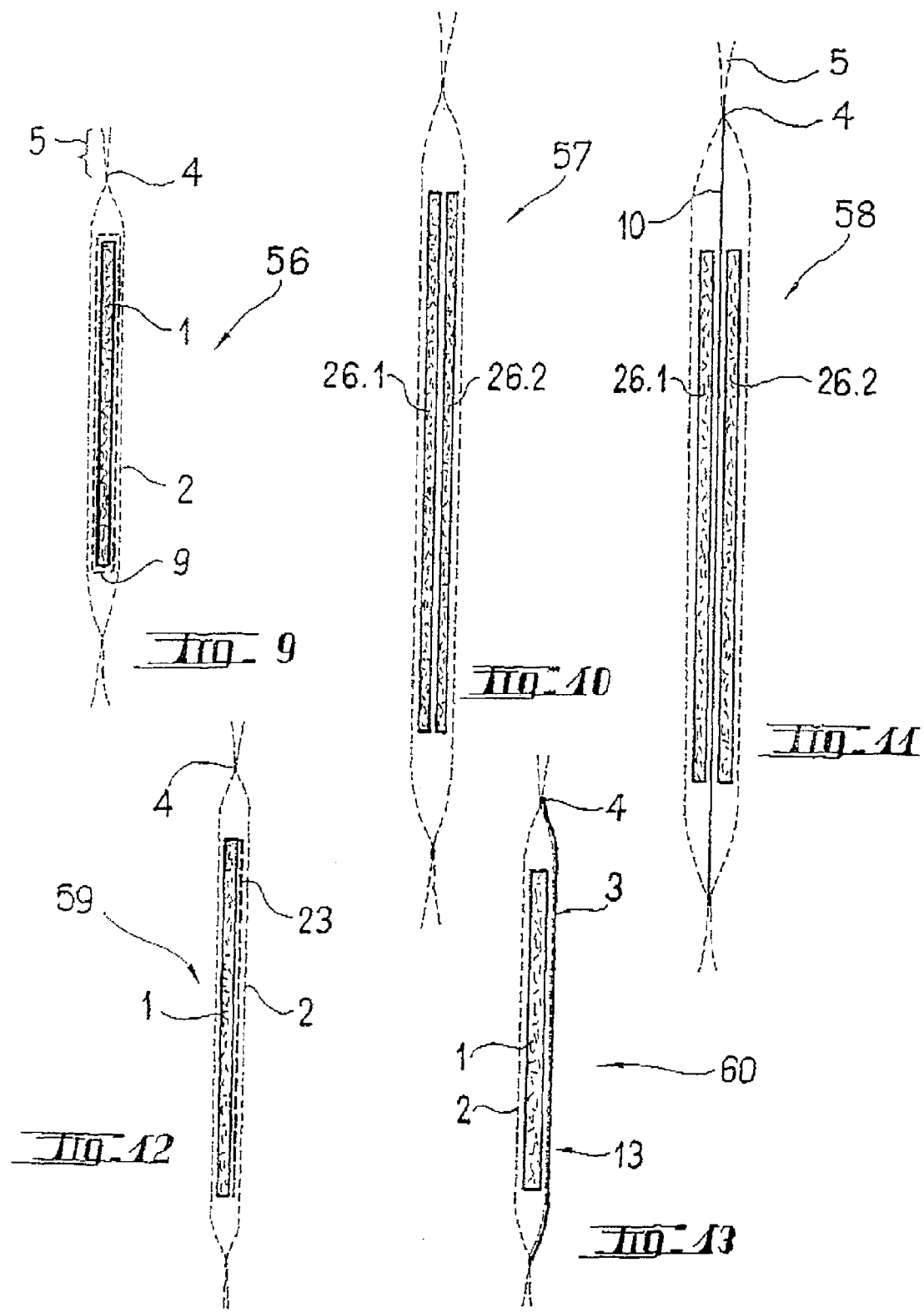

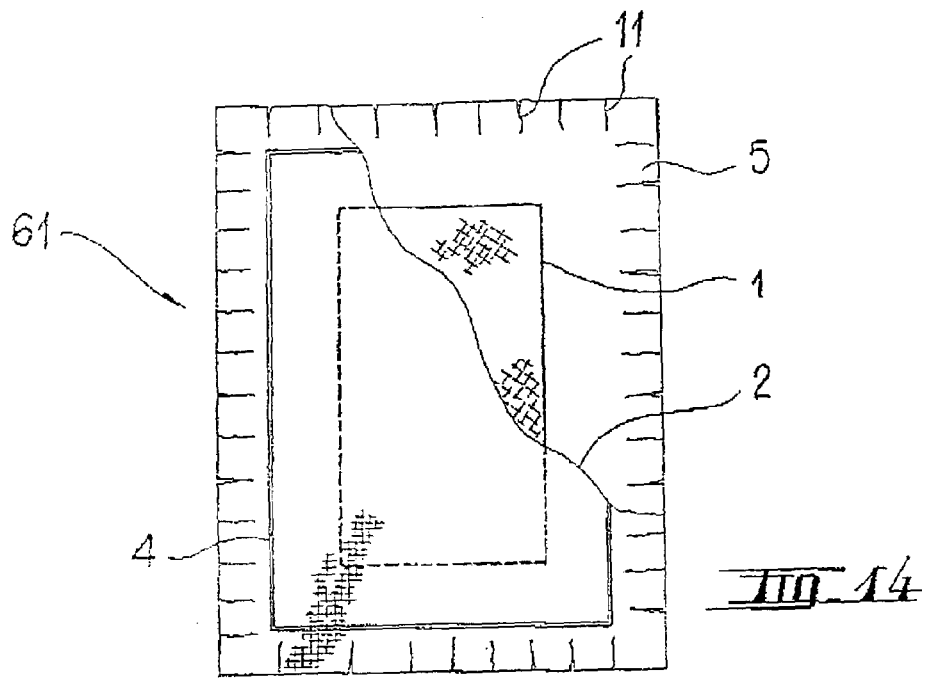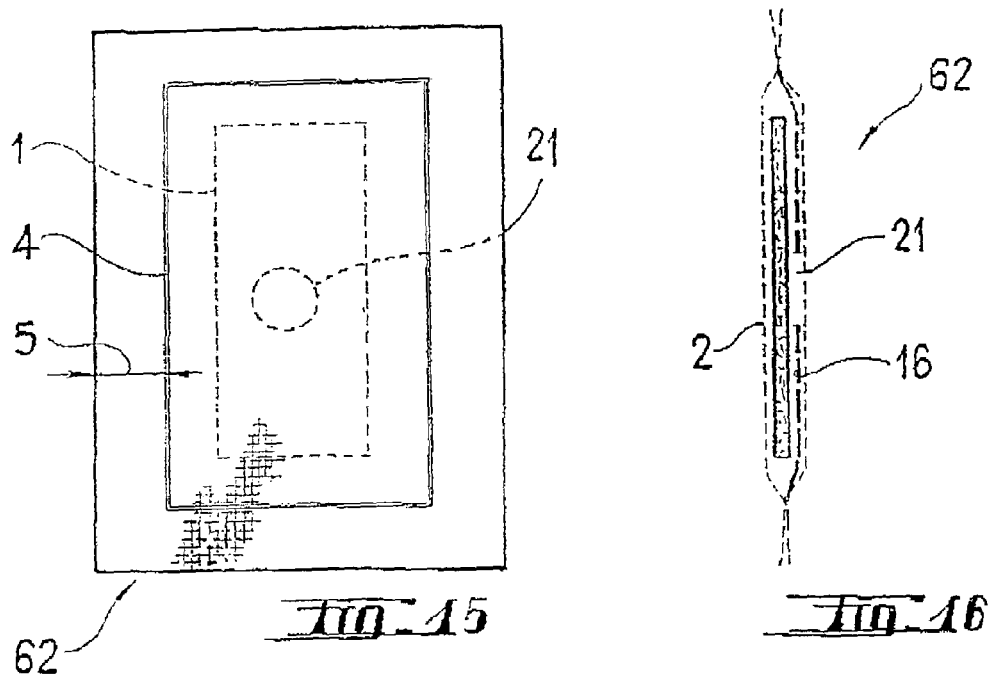

ABSORPTION BODY FOR ATTACHMENT TO THE HUMAN BODY

BACKGROUND OF THE INVENTION

The invention relates to an absorptive body for attachment to the human body, particularly for the purpose of absorbing fluids exiting the human body from such points as wounds, that includes:

An essentially flat material section of absorptive material consisting of an absorptive fleece with super-absorber particles embedded in it, and A moisture-permeable shell surrounding the absorptive material and forming a barrier against particulate elimination and allowing penetration of other eliminated substances to the material section of absorptive material positioned within the shell, whereby the shell is at least partially surrounded by a seam.

An absorptive body of this type is known from DE-OS 100 59 439. It includes a shell with absorptive material positioned within it. The absorptive material is present in the form of a textile fleece material based on cellulose in which a quantity of super-absorber granules is distributed. The total absorptive capacity of the tightly-packed material cannot be used to full advantage because it is not surrounded by the shell. Resultantly, the number of absorptive bodies used with the patient is relatively high since they often must be exchanged. This applies, for example, to colostomy and ileostomy patients who must receive expensive post-operative care.

Another disadvantage of this known absorptive body is that the super-absorber particles released from the absorptive material may also reach the outside when the absorptive body is not in use. This complicates the sterilization process of the absorptive body.

A further disadvantage of the known absorptive body is that the surrounding welded seam stiffens the absorptive body at its edge, and may have a negative influence on the patient's skin tissue, especially at the edges of swollen, inflamed wounds.

SUMMARY OF THE INVENTION

It is the object of the invention to provide an improved low-cost absorptive body of the above-mentioned type that offers the option of taking full advantage of the absorption capacity of the absorptive material.

This object, as well as other objects which will become apparent from the discussion that follows, are achieved, in accordance with the present invention, by providing that the material section of the absorptive body, when seen from above, includes a surface which, in its unwetted state, is 3% to 75% smaller than the surface of the shell when laid flat, and which is positioned within the shell to move freely or be affixed, and by providing that the shell includes pores across its entire surface, each of which is smaller than the unwetted super-absorber particles.

The body locations contemplated by this absorptive body generally include areas for wounds to the skin or mucous membrane, and/or to wound surfaces.

The shell preferably includes a fine-mesh structure whose pores are between 0.05 to 1.0 mm, and preferably between 0.20 and 0.50 mm. The pores are thus smaller than the unincorporated super-absorbers that may remain within the shell.

The pores or meshes may be limited by the threads or fiber sections which possess a cross-section through the shell approximating an arch with the legs of the arches extending outward.

The shell is preferably made of a textile material of soft texture, e.g., from synthetic, ultra-thin, medically-neutral fleece material. The soft structure of the material contributes to a gentle treatment of the wound since the free edges on the overlap of the shell may be deformed or bent upon contact with the wound. Perforated or mesh-type hydrophobic fleece-type film such as polyethylene or polypropylene film or a natural-fiber fabric or fleece impregnated with substances such as silicon, paraffin, wax, or similar that the skin can withstand. The shell material is preferably stretchable at least along one direction.

The absorptive material positioned within the shell may be formed from a plastic fabric or fleece, e.g., from cellulose fibers.

The known so-called super-absorber may, for example, be in the form of a granulate based on a sodium acrylate-acrylic acid-polymerisate that is finely distributed within the carrier matrix, i.e., into cellulose-type material sections.

The absorptive material may also be of gel or sponge type. It is also conceivable to use a flat, sponge-like form as absorptive material that is of open-pore design that is impregnated with a hydro-gel. The absorptive material, including hydro-gel, may be enriched with wound-healing material, e.g., with fever-reducing enzymes from the protease group, or with peptides and/or antibiotics. For this, it is recommended to use a hetero-poly-saccharide such as Agar-Agar or other biologically compatible substances.

The flat absorptive body may be oval, round, polygonal, or trapezoidal.

The surface of the material section is preferably 20% to 35% smaller than the surface of the shell, whereby the latter is limited by the surrounding seam.

It is of great advantage for the shell, viewing the flat side from above, to possess a surrounding overlap that extends over the seam so that the absorptive body is free of hard, sharp edges and corners, and damage to the patient's tissues may largely be prevented at each moment of the absorption process.

A large number of cuts may be cut into the overlap that are preferably slightly shorter than the width of the overlap. This measure contributes to the fact that the outer edges of the overlap can give even further. Moreover, the overlap and/or the surrounding seam may be rounded in the corner areas of the absorptive body.

The absorptive material may consist of two or more layers positioned to lie flat within the shell that possess either the same or different absorptive power. Further, an inner wall may be positioned between the layers that either totally or partially separates the layers from one another.

Both the shell and the absorptive material positioned within the shell may be provided with an odor-suppressing and/or neutralizing or masking additive, e.g., with an activated charcoal filter or with additives with which active nitrogen or sulfur/hydrogen compounds, for example, may be removed from the gaseous milieu.

Odor-suppressing materials may include natural substances or extracts, bio-inert materials, or plastics that possess a specific electronic negativity under which a deposit and combining of sulfur/hydrogen compounds may result. For this, the plastic molecules possess specific geometric shapes such as prisms or spirals.

Overall, the absorptive material so positioned, as well as the shell described above, are in the position to create an inner micro-climate that promotes healing.

An additional inner shell of an absorptive material such as cotton or cellulose may be positioned between the absorptive material and the shell whose ability to absorb is low, or is less than that of the absorptive material. Such an inner shell makes direct contact between the mucous-membrane cells at the wound or body cavity and the absorptive material more difficult. In this manner, one achieves the fact that the secretions may be at least partially distributed in a controlled manner.

Instead of an intermediary layer with limited absorptivity, a film permeable to fluids may be used that is also provided with at least one aperture. In this case, it is recommended to adhere the film to the shell.

The absorptive material may consist of two or more layers positioned flat within the shell that possess the same or different degrees of absorptivity. Further, an inner wall may be positioned between the layers that partially or completely separate the layers from one another.

Further, a fluid-permeable film section may be mounted on at least one outer side of the fluid-permeable shell.

The shell and/or the absorptive material may have a substance such as an adhesive that adheres to the patient's body provided on its circumference. Suitable adhesives include, for example, pectin/cellulose compounds. The substance to be sealed off must, however, allow for the simple removal or pulling off of the For a full understanding of the present invention, reference should now be made to the following detailed description of the preferred embodiments of the invention as illustrated in the accompanying drawings.

BRIEF DESCRIPTION OF THE DRAWINGS

FIG. 4 shows the flat side of a trapezoidal absorptive body as seen from above.

FIG. 5 shows the flat side of a square absorptive body as seen from above.

FIG. 6 shows another embodiment of the absorptive body.

FIG. 8b is a perspective view of the absorptive body per FIG. 8a.

FIGS. 9-13 are schematic cross-section views of other embodiment shapes of the absorptive body.

FIG. 14 shows the flat side of a square absorptive body with cuts in the overlap as seen from above.

FIGS. 15 and 16 show, respectively, the flat side of the absorptive body per FIG. 12 with an inner aperture, and a cross-section thereof.

DESCRIPTION OF THE PREFERRED EMBODIMENTS

Figure 1:
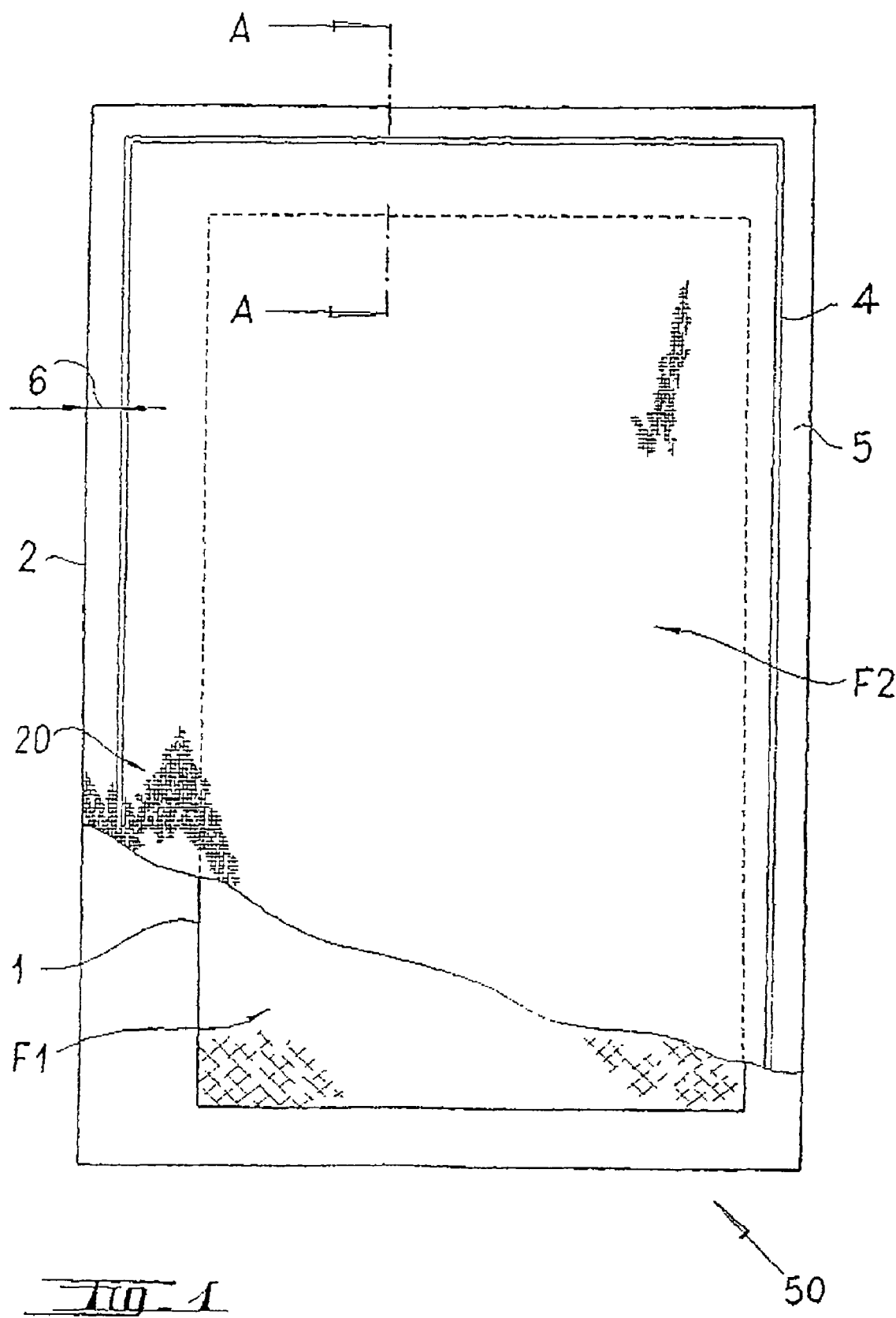
FIG. 1 shows the flat side of a rectangular absorptive body as seen from above.

The preferred embodiments of the present invention will now be described with reference to FIGS. 1-22 of the drawings. Identical elements in the various figures are designated with the same reference numerals.

FIG. 1 shows a absorptive body 50 that consists of a shell 2 and absorptive material 1 in the form of a flat cellulose-type material section loosely placed into it. The material section possesses a thickness of about 2 mm, and is impregnated with super-absorber granulate. The dimensions of the material section are:

Length 15.5 cm,
Width: 9.0 cm;
Thickness: 2.0 mm.

The shell 2 per FIG. 1 is made of two equal sidewalls 2.1, 2.2 connected together at their peripheries by means of a weld seam 4. The dimensions of the material shell 2 are:

Length 19 cm,
Width: 10 cm;
Measured between the opposing seams.

Resultantly, the surface area F1 is about ⅔ of the surface area F2.

The full absorptive capability of the absorptive material may be fully developed by means of the advantageous geometric ratios between the areas F1 and F1 of the shell 2 and of the absorptive material 1.

The shell 2 includes a fine-mesh structure whose pores 20 in this case are about 0.15 mm to 0.25 mm.

Figure 3A:
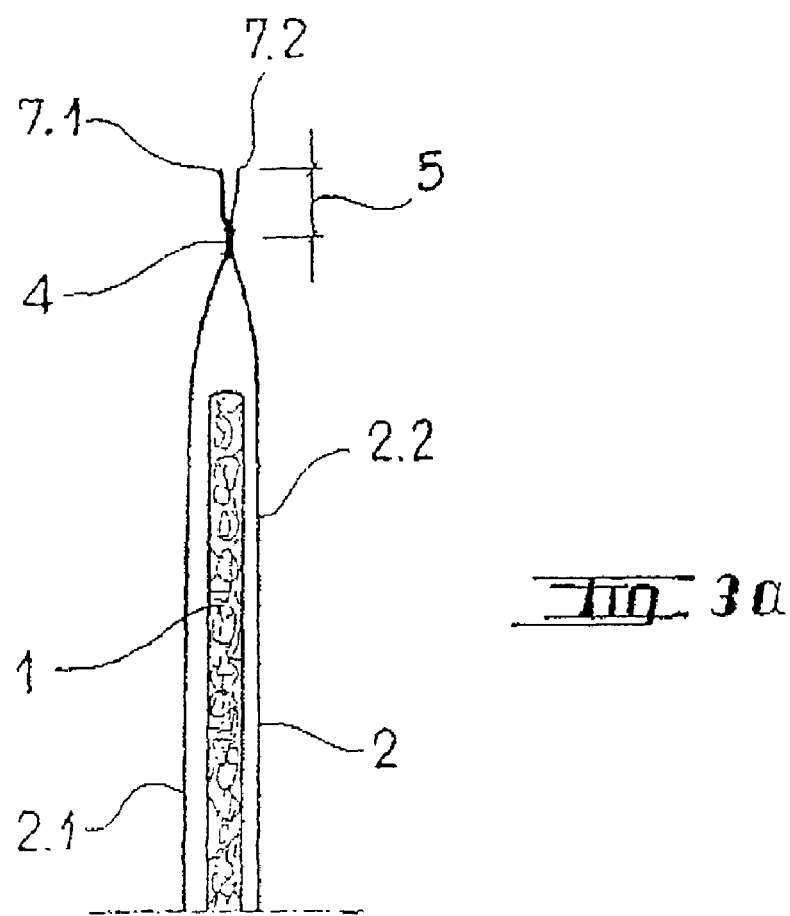
FIGS. 3a and 3b show part of the absorptive body along projection A-A per FIG. 1.
Figure 3B:
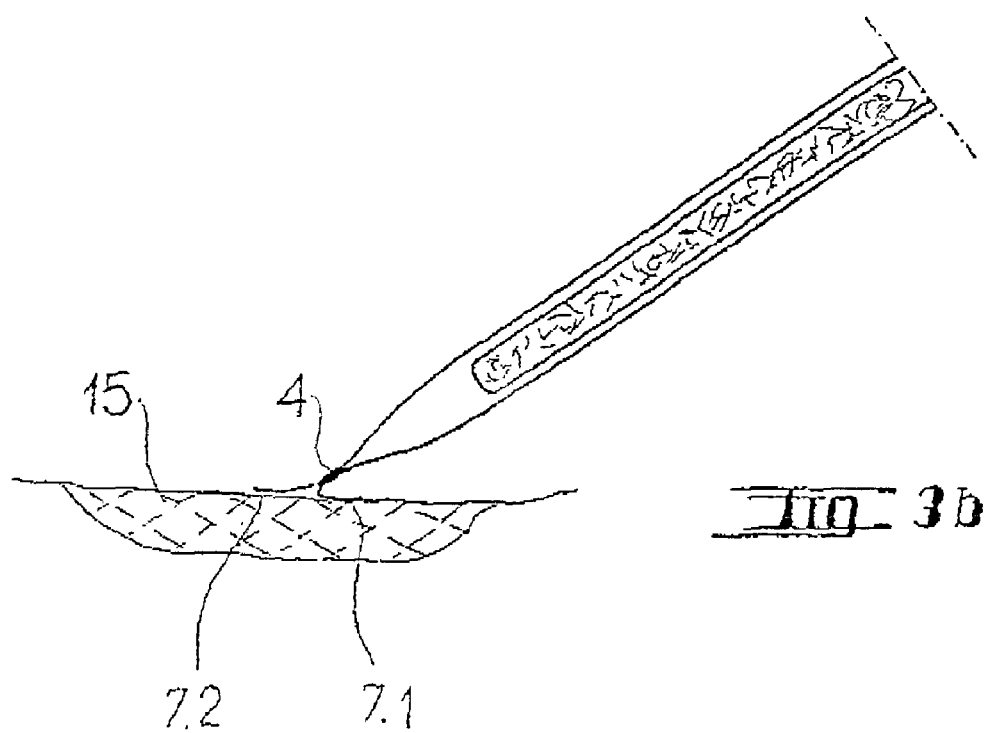

A peculiarity of the absorptive body 50 is a surrounding overlap 5 extending out over the weld seam 4 whose width 6 (see FIG. 1) is between 4 mm and 5 mm. The task of the overlap 5 is to form a soft buffer zone between the patient's tissue such as an open wound 15 (see FIG. 3b) in case the absorptive body is handled with insufficient care, i.e., if the edge or corner of the absorptive body touches the sensitive wound. FIGS. 3a and 3b show that the free outer edges 7.1 and 7.2 of the shell at the overlap 5 contain no stiff areas. Rather, the outer edges 7.1 and 7.2 are deformed as shown in FIG. 3b. The outer edges 7.1 and 7.2 spread apart, or gently deploy in one direction so that the wound 15 is protected from contact with the seam (particularly with an absorptive body that is positioned edgewise or obliquely).

It is suggested that other shells, particularly square shells with an overlap 5, e.g., with dimensions of 5.0 cm×5.0 cm or 7.0 cm by 7.0 cm be used in which the surface of the inner absorptive material section is correspondingly smaller (see FIG. 5).

Figure 22:
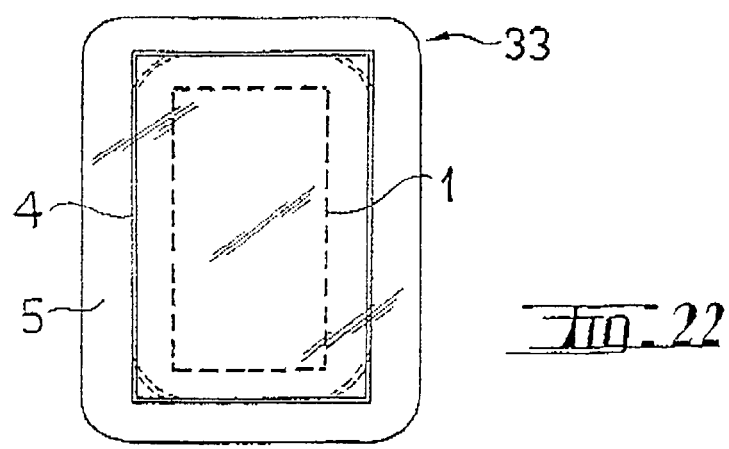
FIG. 22 shows the flat side of a square absorptive body with rounded corner sections as seen from above.

FIG. 22 shows a flat absorptive body whose overlap 5 is gently rounded at the corner areas 33. Dotted lines depict a rounding of the seam 4 in the corner areas 33.

Figure 2:
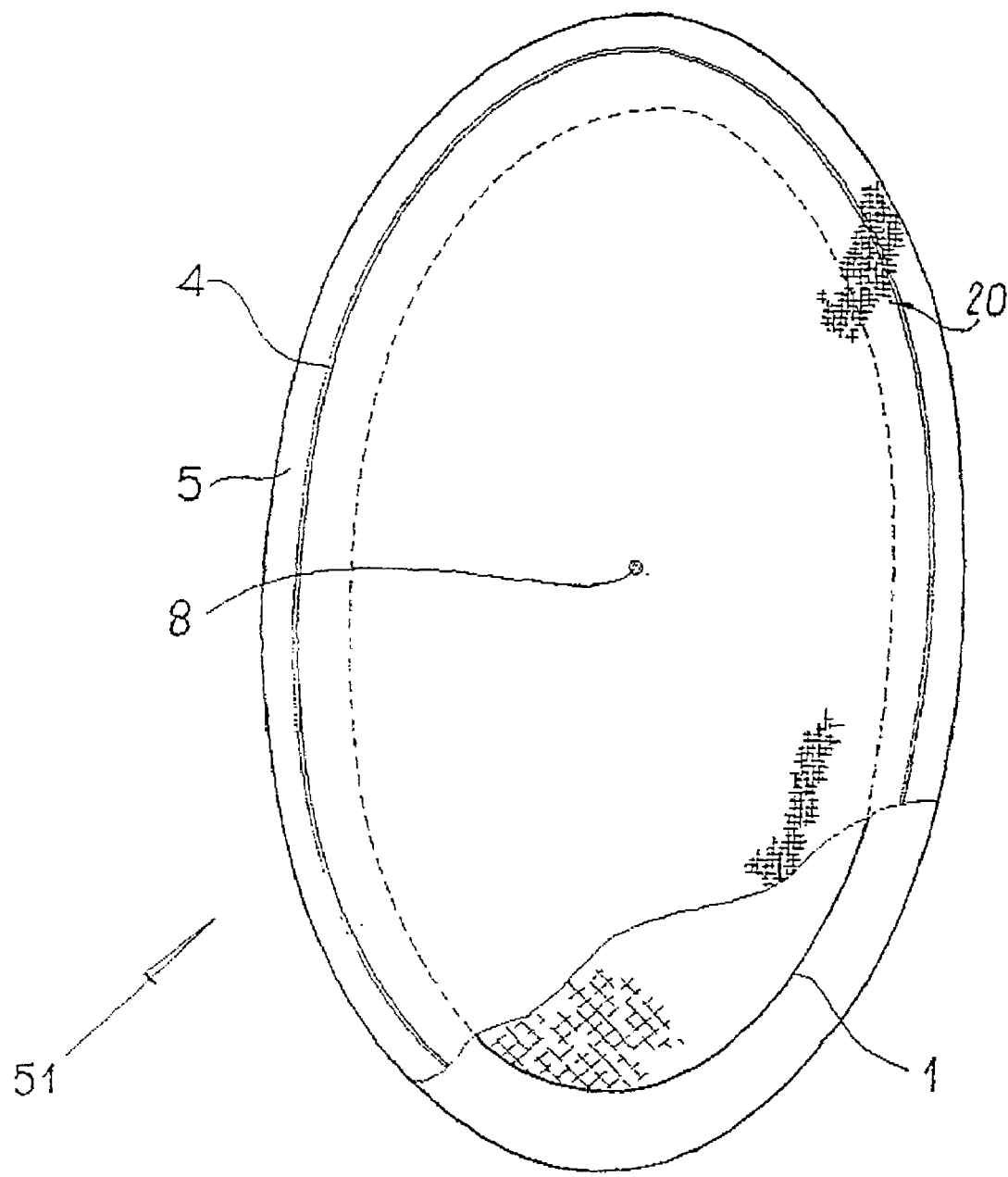
FIG. 2 shows the flat side of an oval absorptive body as seen from above.

FIG. 2 shows an elliptical absorptive body 51 in which the absorptive material 1 is attached to the shell 2 by means of a single, central adhering point 8. The absorptive material may not be separated from the shell 2. Medically suitable adhesive substances or mixtures may be used as adhesives that dissolve upon swelling of the absorptive material (not shown).

FIG. 4 shows a trapezoid-shaped absorptive body 52 into whose shell 2 a section of the above-described textile absorptive material with super-absorber has been placed. The one-piece manufactured shell 2 is folded along the trapezoid base edge 28, and is welded together at the other edges. In the present case, the shell does not include an overlap extending past the weld seam. Since the surface area F1 of the textile absorptive material is significantly smaller than the surface area F2 of the shell, the absorption process may proceed unhindered.

FIG. 6 shows a deviating embodiment example of the absorptive body (reference index 53) in which the height (H) of the rectangular material section corresponds to the separation between two opposing seams, and in which the width of the shell is greater than the width of the material section. The displaceability of the inner material section is ensured only along direction X.

Figure 7:
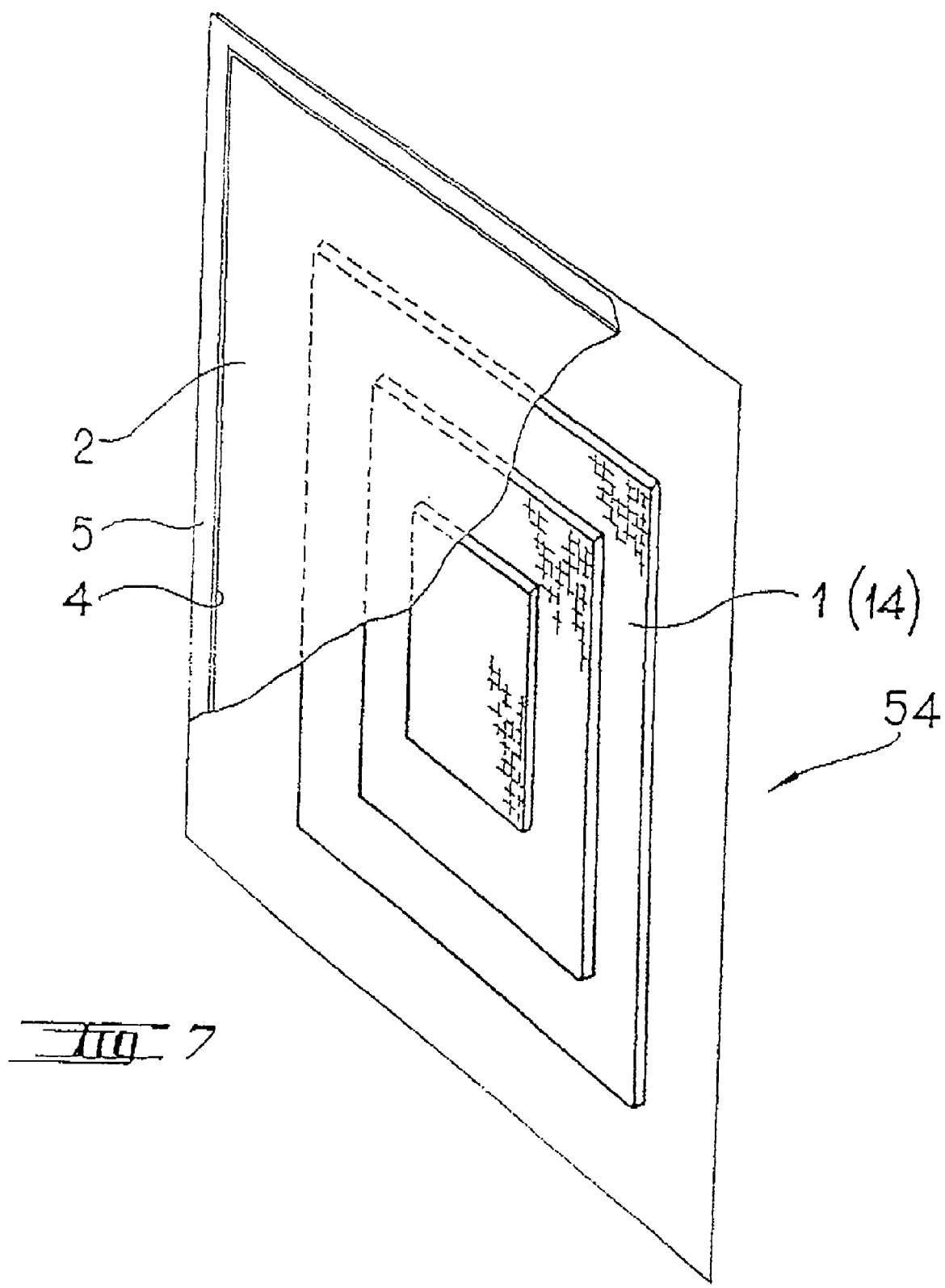
FIG. 7 is a perspective view of an absorptive body with absorptive material in the form of a multi-dimensional body.
Figure 8A:
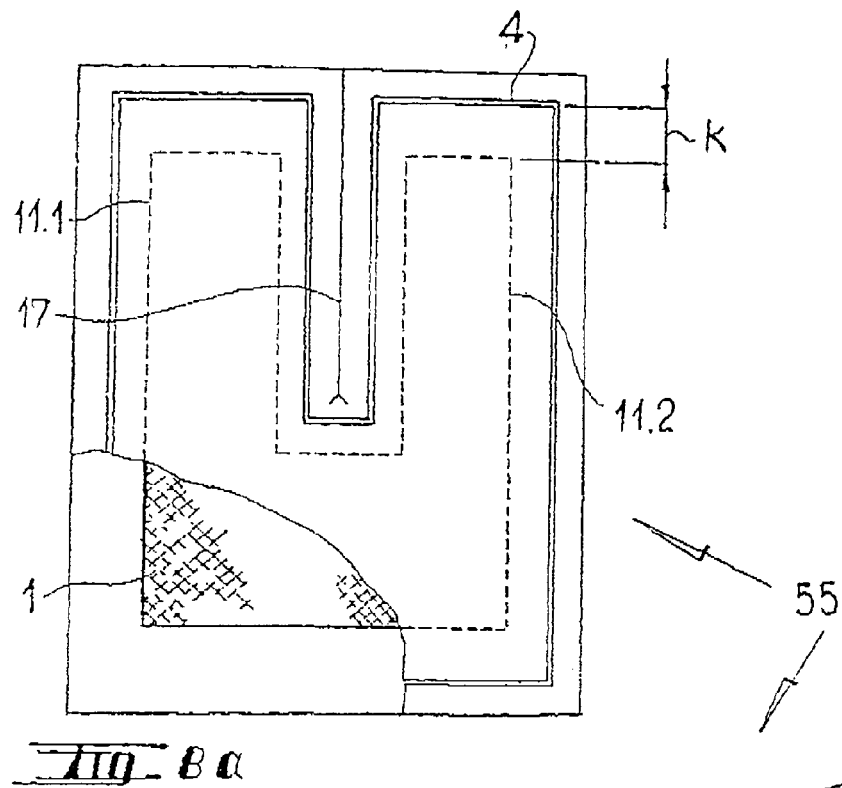
FIG. 8a shows the flat side of an absorptive body with wings as seen from above.
Figure 8B:
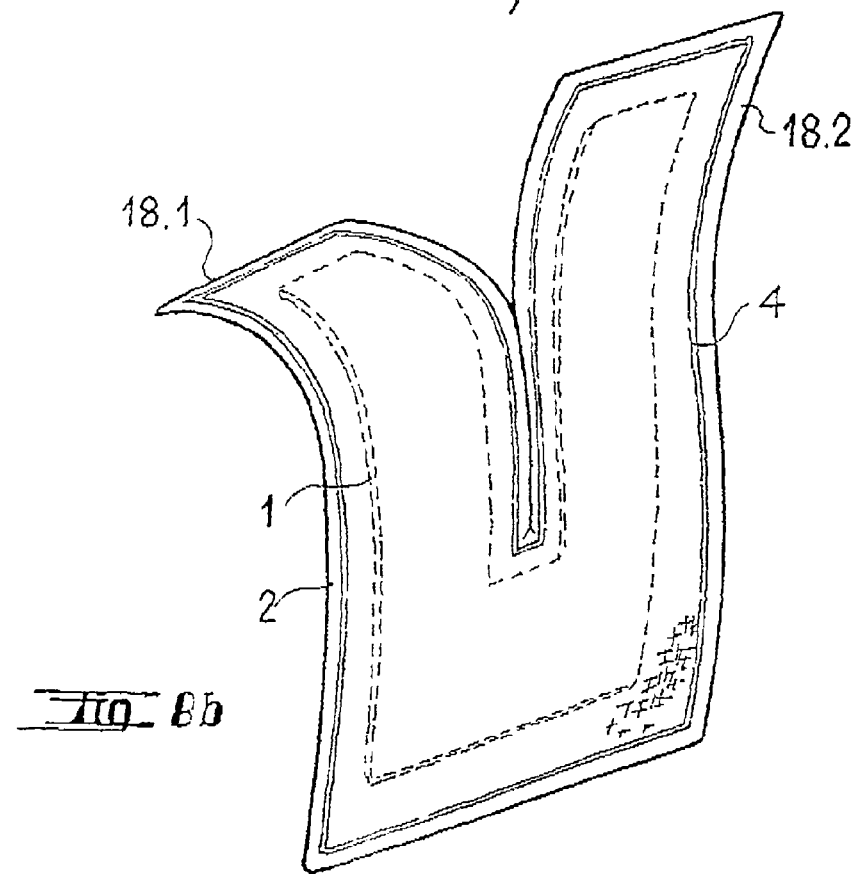

FIG. 7 shows that an absorptive material 1 free to move may be used instead of the flat one in the shape of a prismatic body 14 that may be adapted to any raised and/or recessed part of the wound. The body 14 consists of several absorptive material sections overlaid in a pyramid fashion and connected by at least a spot weld. These material sections may possess the same, or differing, degrees of absorption. Any number of prismatic shapes of the freely-moving absorptive material 1 are conceivable. Overall, the absorptive body 54 shown in FIG. 7 are also flat, but somewhat thicker than the individual absorptive bodies 50; 51; 52 and 53.

In another embodiment example (reference index 55; see FIGS. 8a and 8b), an absorptive body is involved whose shell 2 includes a cut line 17 to the center that is positioned perpendicular with respect to the seam 4 or the overlap, and a portion of the absorptive body is divided into two flexible wings 18.1, 18.2.

The wing-shaped form allows placement of the absorptive body around a drain or tube-type exit point. The absorbing material section 1 in this case is U-shaped, whereby each of its two U arms 11.1 and 11.2 are completely surrounded by the seam and the overlap. Instead of the cut line, a U- or V-shaped section may be removed (not shown).

FIG. 9 shows an absorptive body 56 with an inner shell 9 that completely surrounds the absorptive material 1 (super-absorber). The surrounding shell 9 is made of a fluid-absorptive material whose ability to absorb is less than that of the inner absorptive body 1. The surrounding shell 9 is in turn surrounded by the outer shell 2 with overlap 5.

FIG. 10 shows an absorptive body (reference index 57) in which the absorptive material consists of two layers 26.1, 26.2, of a super-absorber whereby they are distinguished from each other by degree of absorption.

In a similar embodiment example (see FIG. 11), an absorptive body 58 is involved that includes a fluid-permeable separating wall dividing the absorptive body into two chambers 21.1, 21.2. A layer 26.1; 26.2 is positioned within each chamber 21.1, 21.2.

FIG. 12 shows an absorptive body 59 with an inner intermediary layer 23. The intermediary layer 23 made of cotton includes a smaller degree of absorptivity than that of the absorptive material 1 itself, and has the task of preventing contact between the mucous-membrane cells of the wound and the absorptive material.

As FIG. 13 shows, a fluid-permeable film layer 3 is positioned on an outer side 13 of an absorptive body 60. The film section 3 is preferably transparent, and extends over the entire surface limited by the surrounding seam 4 but excluding the overlap 5. Nearly all above-mentioned embodiment examples are suited to manufacture the absorptive body 60 (except reference index 58).

An absorptive body 61 shown in FIG. 14 distinguishes itself by several cuts 11 that are placed in the overlap 5 and positioned about its periphery. Thus, a "greased" overlap 5 is formed whose outer edges may give even more.

FIGS. 15 and 16 show another absorptive body (reference index 62) whose design is a further development of the embodiment example shown in FIG. 12. A intermediary layer 16 surrounding the seam includes central, round aperture 21 that has the task of better distributing the incoming secretions. The cotton intermediary layer 16 also possesses a smaller degree of absorptivity that of the absorptive material 1 itself. Instead of an absorptive one, a fluid-permeable, e.g., film-type intermediary layer (not shown) with the aperture 21 may be provided.

Figure 18:
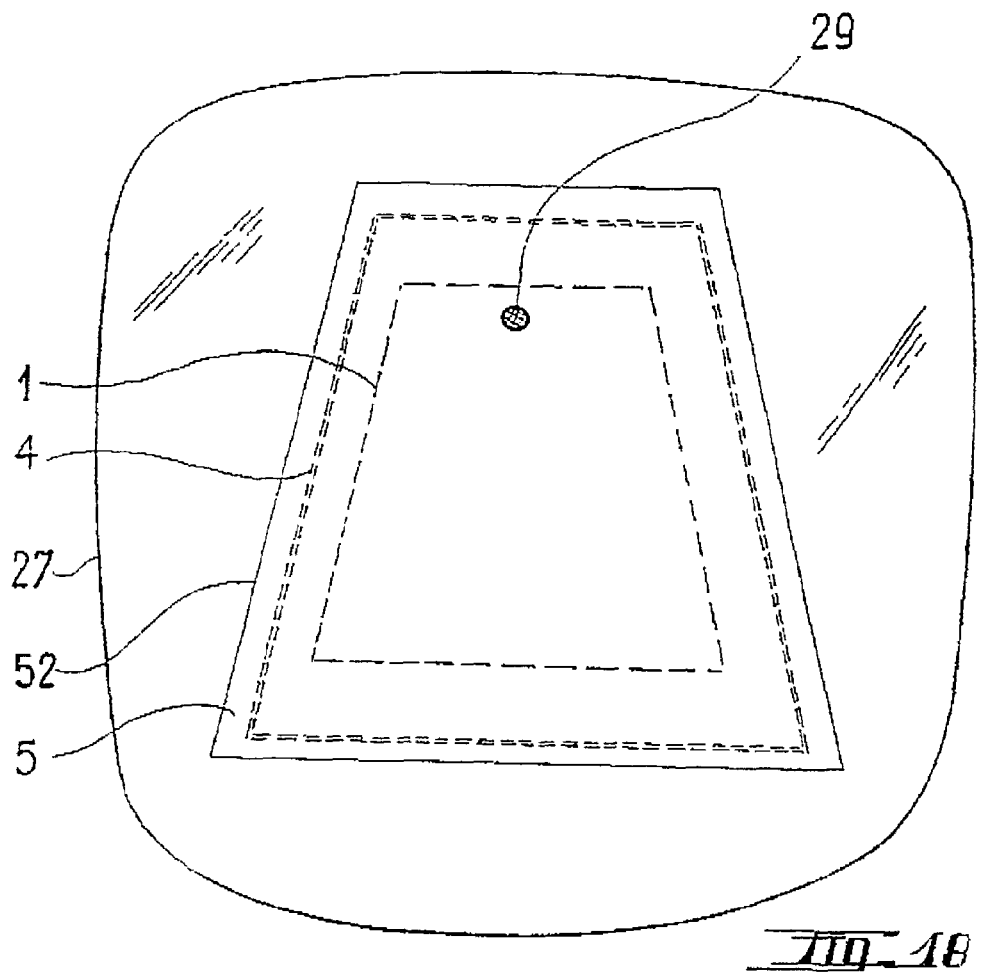
FIG. 18 is a schematic view from above of the flat side of a trapezoidal absorptive body per FIG. 4, inserted into a colostomy bag.

FIG. 18 shows the positioning of a trapezoid-shaped absorptive body 52 within a schematically-indicated colostomy bag 27. The absorptive body 52 is to be attached to the colostomy bag via a button-like fastener. A biologically compatible adhesive is best suited for adhesion. This attachment may be releasable.

Figure 19:
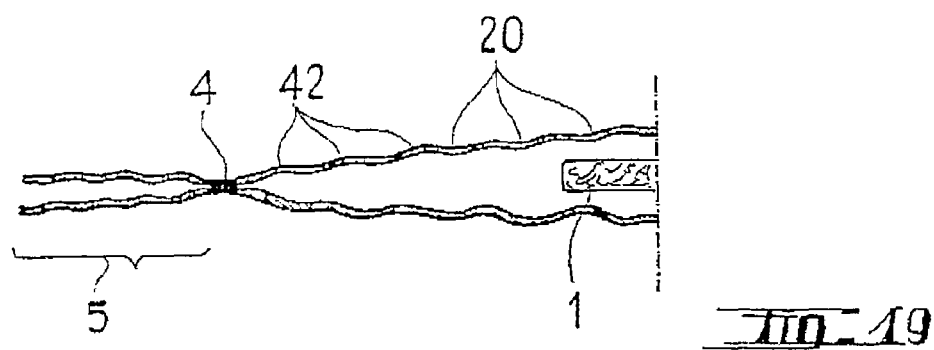
FIG. 19 is a partial cutaway view through the absorptive body of FIG. 18 in the seam area.

FIG. 19 shows an enlarged partial cutaway through the shell 2 in the area of the overlap 5 and the surrounding seam 4. The smooth, hydrophobic material of the shell 2 includes numerous, gently-sloping arches 42 directed outward that lie between the pores 20. This material structure of the shell achieves the fact that the fluid glides over the surface of the shell, and may pass through the pores more easily into the interior of the absorptive body.

Figure 17:
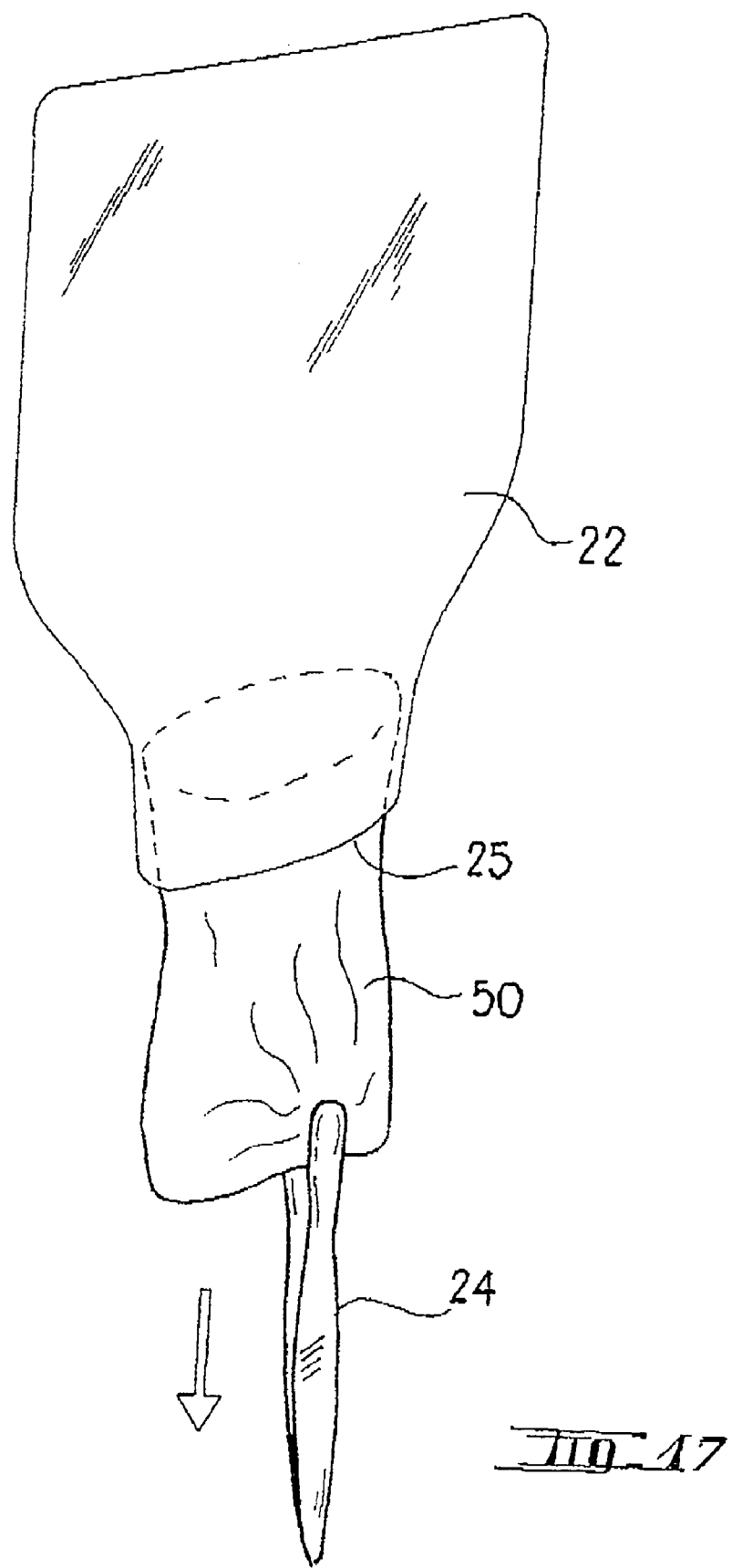
FIG. 17 is a perspective view of the absorptive body per FIG. 1 being stripped from an ileostomy bag.
Figure 20:
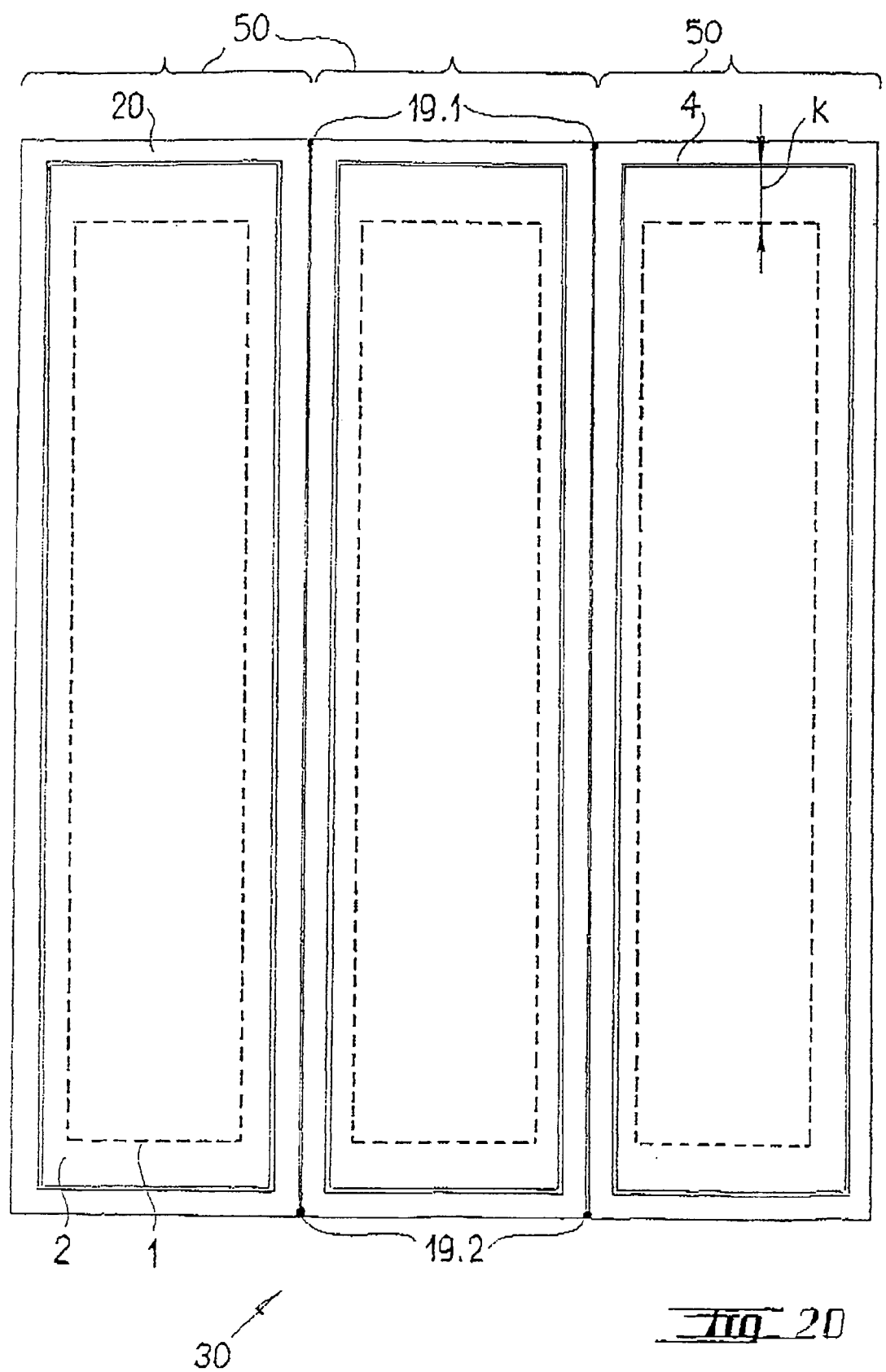
FIG. 20 is an ensemble consisting of three absorptive bodies.

Further, FIG. 20 shows an ensemble 30 consisting of three flat, rectangular absorptive bodies 50 each of which is about 20 cm long and about 3 cm to 4 cm wide. The overall result is a flat shape that may be inserted into a conventional ileostomy bag. Since the absorptive bodies 50 are welded together only at two bodies may be grabbed using forceps 24 via an available aperture, and may be separated and extracted. Thus, adequate free space k between the material section 1 and the seam 4 is ensured so that manipulation with the forceps may be simplified. FIG. 17 shows a ileostomy bag 22 from which a used absorptive body 50 is removed at its lower opening 25 by means of the forceps 24.

Figure 21:
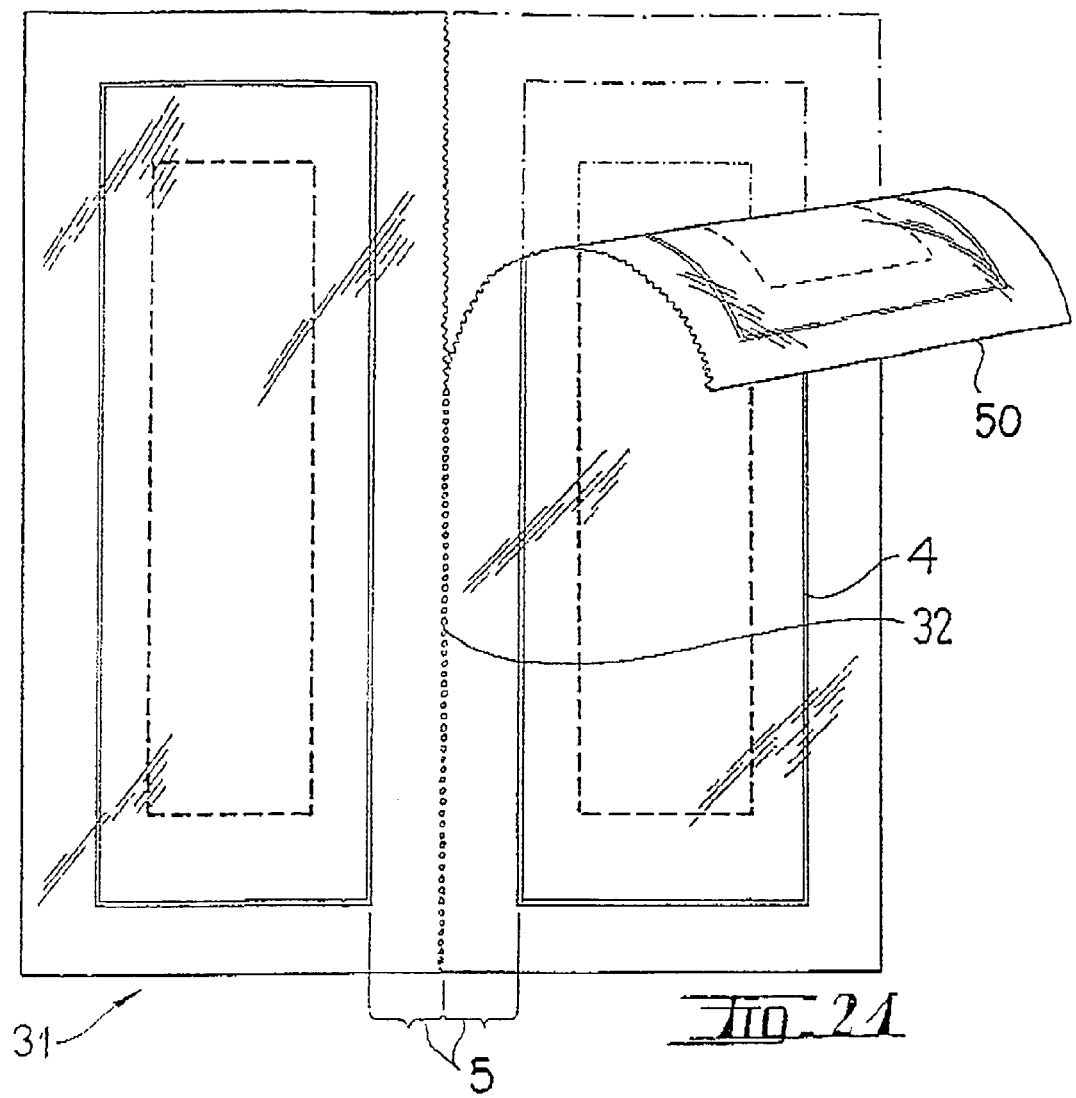
FIG. 21 is an ensemble consisting of two absorptive bodies connected to each other via a tearable perforation line.

Finally, FIG. 21 shows a further ensemble 31 consisting of two equally flat, rectangular absorptive bodies 50 connected to each other via a penetrating perforation line 32. The perforation line 32 allows simple separation of the two absorptive bodies from each other. As FIG. 21 shows, the perforation line 32 runs exactly along the centerline between the seam sections of the absorptive body while maintaining the provided overlaps 5. This enables trained personnel to rip the product to the center, for example, of the perforation line 32 and to place it around a tubular line. The ensemble may be folded together along the perforation line 32.

The absorptive body or ensemble based on the invention is preferably sold as a sterile product sealed within an air tight package.

There has thus been shown and described a novel absorptive body for attachment to the human body which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

The invention claimed is:

1. An absorptive body for attachment to the human body, particularly for the purpose of absorbing fluids exiting the human body from a wound, said absorptive body comprising:
   (a) an essentially flat material section of absorptive material having an absorptive surface area on at least one side, said absorptive material including an absorptive fleece with super-absorber particles embedded in it; and
   (b) a moisture-permeable shell having an external surface area covering the absorptive surface area of the absorptive material and forming a barrier against solid excretions from a wound while allowing liquid substances from the wound to penetrate into the absorptive material, said shell having a seam in the surface area thereof which surrounds the material section to seal the material section within the shell;
   the improvement wherein the absorptive surface area of the material section, in its unwetted state, is 3% to 75% smaller than the external surface area of the shell when laid flat, wherein the shell includes pores across its external surface area, each of which is smaller than the super-absorber particles, in an unwetted state, and wherein the external surface area of the shell has an overlap area extending outward, with respect to the absorptive material, beyond the seam at every point around the seam.

2. Absorptive body as in claim 1, wherein the absorptive body is free of hard, sharp edges or corners.

3. Absorptive body as in claim 1, wherein the pores of the shell are limited by thread or fiber sections which have a cross-section through the shell approximating an arch with legs of the arch extending outward.

4. Absorptive body as in claim 1, wherein the shell has at least one cutout or cut line that divides a portion of the absorptive body into at least two flexible wings.

5. Absorptive body as in claim 4, wherein the cutout or line is oblique to the seam.

6. Absorptive body as in claim 4, wherein the cutout or cut line is perpendicular to the seam.

7. Absorptive body as in claim 4, wherein the cutout or cut line extends to the center of the absorptive body.

8. Absorptive body as in claim 4, wherein the cutout or cut line is surrounded by the seam that extends and connects to the rest of the seam.

9. Absorptive body as in claim 1, wherein the flat side of the material section, in top view, is one of a U-shape and W-shape.

10. Absorptive body as in claim 1, wherein an additional inner shell of absorptive material is positioned between the absorptive material and the shell, the absorptivity of the additional inner shell being less than that of the absorptive material itself, whereby direct contact between the mucous-membrane cells at the wound or body cavity and the absorptive material is limited.

11. Absorptive body as in claim 1, wherein an additional, inner intermediary layer in the form of a material section of absorptive material positioned between the absorptive material and the outer shell, whereby direct contact between the mucous-membrane cells at the wound or body cavity and the absorptive material is limited.

12. Absorptive body as in claim 1, wherein a fluid-permeable film section is positioned on at least one outer side of the entire surface of the perforated shell.

13. Absorptive body as in claim 1, wherein the shell surrounds two flat-lying layers of the absorptive material that have a same or different degree of absorptivity.

14. Absorptive body as in claim 13, wherein the layers are separated from each other by an interior wall.

15. Absorptive body as in claim 1, wherein its exterior dimensions are so selected that it may be extracted from a lower opening of an ileostomy bag after use.

16. Absorptive body as in claim 1, which is loosely affixed to at least one other absorptive body positioned adjacent to it, whereby the inter-connected absorptive bodies may be separated from each other by hand.

17. Absorptive body as in claim 16, wherein one overlap or seam is attached together at at least one connection point with the adjacent absorptive body.

18. Absorptive body as in claim 16, which is connected by means of a perforation line with the adjacent absorptive body so that it may at least partially be torn apart.

19. Absorptive body as in claim 1, which includes at least one affixing point by means of which the absorptive body may be affixed within a serviceable container.

20. Absorptive body as in claim 10, wherein said additional inner shell is made of a material selected from the group consisting of cotton and cellulose.

21. Absorptive body as in claim 11, wherein said additional intermediary layer is made of a material selected from the group consisting of cotton and cellulose.

* * * * *